(12) United States Patent
Vitullo et al.

(10) Patent No.: US 6,641,563 B1
(45) Date of Patent: Nov. 4, 2003

(54) STYLET-FREE EPIDURAL CATHETER AND THREAD ASSIST DEVICE

(75) Inventors: Jeffrey M. Vitullo, Pottstown, PA (US); Carl Botterbusch, Wyomissing, PA (US); Don Ulrich, Denver, PA (US)

(73) Assignee: Arrow International, Inc., Reading, PA (US)

( * ) Notice: Subject to any disclaimer, the term of this patent is extended or adjusted under 35 U.S.C. 154(b) by 113 days.

(21) Appl. No.: 09/703,892

(22) Filed: Nov. 1, 2000

(51) Int. Cl.$^7$ .............................................. A61M 5/178
(52) U.S. Cl. ....................... 604/158; 604/264
(58) Field of Search ................. 604/523, 264, 604/27, 40, 44, 48, 512, 104, 115, 158, 161, 164.01, 164.03, 164.04, 164.07, 164.09, 164.13, 165.01, 170.03, 167.06, 272–274, 524, 525, 117, 246, 534–536, 249, 256, 905; 285/24, 27, 34, 90

(56) References Cited

U.S. PATENT DOCUMENTS

| | | | | |
|---|---|---|---|---|
| 3,856,009 A | * | 12/1974 | Winnie .................. 604/170.03 |
| 4,349,023 A | * | 9/1982 | Gross ......................... 604/158 |
| 4,645,491 A | | 2/1987 | Evans | |
| 5,002,535 A | * | 3/1991 | Gross ......................... 604/272 |
| 5,004,456 A | * | 4/1991 | Botterbusch et al. ....... 604/158 |
| 5,062,836 A | * | 11/1991 | Wendell ................ 604/167.04 |
| 5,190,529 A | * | 3/1993 | McCrory et al. ........... 604/175 |
| 5,191,888 A | * | 3/1993 | Palmer et al. .............. 600/434 |
| 5,234,002 A | * | 8/1993 | Chan ......................... 600/585 |
| 5,263,936 A | * | 11/1993 | Yurino ....................... 604/158 |
| 5,312,375 A | * | 5/1994 | Gurmarnik ................. 604/158 |
| 5,368,573 A | * | 11/1994 | Andrew ...................... 604/158 |
| 5,658,309 A | * | 8/1997 | Berthiaume et al. ........ 606/192 |
| 5,700,251 A | * | 12/1997 | Miyauchi et al. ...... 604/167.01 |
| 5,791,036 A | | 8/1998 | Goodin et al. | |
| 5,836,914 A | * | 11/1998 | Houghton .................. 604/117 |
| 5,836,916 A | * | 11/1998 | Corn .......................... 604/158 |
| 5,843,048 A | * | 12/1998 | Gross ......................... 604/264 |
| 5,846,226 A | * | 12/1998 | Urmey ....................... 604/158 |
| 5,851,203 A | | 12/1998 | van Muiden | |
| 5,853,391 A | * | 12/1998 | Bell ........................... 604/158 |
| 5,941,853 A | | 8/1999 | Collins | |
| 5,947,940 A | | 9/1999 | Beisel | |
| 5,976,110 A | * | 11/1999 | Greengrass et al. ........ 604/158 |
| 6,106,487 A | * | 8/2000 | Duane et al. ............... 600/585 |

* cited by examiner

Primary Examiner—Brian L. Casler
Assistant Examiner—Cris L. Rodriguez
(74) Attorney, Agent, or Firm—Anster, Rothstein & Ebenstein (57) ABSTRACT

A stylet-free epidural catheter for insertion into a patient via a needle defining proximally a needle hub and distally a needle tip, includes a catheter having a proximal end, a distal end, and a body connecting the ends. The body defines therealong a stiffening section of a predetermined length disposed a predetermined distance proximally of the distal end such that it is located generally about an area where the body approaches a needle hub when the distal end approaches a needle tip. The stiffening section has a flexural stiffness at least twice that of the remainder of the body. A thread assist device to reduce buckling of a catheter being inserted through a needle, includes a body defining a TAD proximal end, a TAD distal end substantially spaced apart along a longitudinal axis from the TAD proximal end, and a TAD sidewall connecting the TAD ends. The TAD distal end is configured and dimensional for at least partial receipt and releasable maintenance within a hub of a needle, and the TAD sidewall is configured and dimensioned intermediate the TAD ends to enable axial sliding manipulation of the catheter through the needle hub by a user. The TAD ends substantially preclude non-axial movement of the catheter at the TAD ends and the TAD sidewall limits non-axial movement of the catheter between the TAD ends.

7 Claims, 7 Drawing Sheets

STYLET-FREE EPIDURAL CATHETER AND THREAD ASSIST DEVICE

BACKGROUND OF THE INVENTION

The present invention relates to a stylet-free epidural catheter for insertion into a patient via a needle, as well as a thread assist device, both to reduce buckling of a catheter in and around the needle hub, and more particularly to a combination of such an epidural catheter and such a thread assist device.

Commonly assigned U.S. Pat. No. 5,947,940 entitled "Catheter Reinforced to Prevent Lumenal Collapse and Tensile Failure Thereof" is incorporated herein by reference. This patent discusses in detail the problems associated with medical catheters, and in particular an epidural catheter, and the need for reinforcement thereof to meet the rigorous requirements of an epidural catheter. The reinforcement disclosed is at least one helical reinforcing member (preferably predominantly non-metallic) wound around the longitudinal axis of the elongated tubular body of the catheter for reinforcing the body to prevent radial collapse thereof during bending and pinching thereof and to prevent longitudinal breakage thereof under tension. Such catheters have proven to be quite satisfactory in use and, in particular, as epidural catheters.

Nonetheless, the design of the catheter described above has proven to be less than totally satisfactory. Typically, the use of a stylet within the catheter is still required during the insertion operation. From the point of view of the catheter manufacturer, this results in additional costs, both for the manufacture of the stylet and for the insertion of the stylet through the catheter. From the point of view of the catheter user, an additional step in the procedure is required to ultimately withdraw the stylet from the catheter after the stylet has served its function of stiffening the catheter sufficiently to allow it to enter the epidural space (the ligamentum flavum). Due to the length of the stylet, this is a time-consuming and laborious operation step. Furthermore, the removed stylet is a contaminated "sharp" which must be safely and specially disposed of in order to not expose room personnel to additional risks of contamination.

The prior art also teaches thread assist devices (TADs) which enter into the luer hub of the needle and preclude buckling (non-axial or lateral collapse) of the catheter just as the catheter distal tip is emerging from the distal end of the needle into the epidural space, a time when buckling tends to occur due to the additional resistance exerted by the ligaments of the epidural cavity. The known TADs preclude buckling of the catheter in the region of the needle hub by completely surrounding the catheter sidewall so that there is no room in which the catheter can buckle. On the other hand, this positioning of the TAD requires a practitioner to move the catheter forwardly through the needle from a point of contact (between the practitioner and the catheter) which is disposed proximally of the needle hub; this makes it more difficult for the surgeon to introduce a substantially straight or linear length of the catheter into the needle hub. At the very time that the practitioner is pressing on the catheter with his fingers and using friction (between his fingers and the catheter) to slide the catheter forwardly through the TAD and the needle, there is a tendency for the practitioner to laterally deflect the catheter before it enters the TAD so that it is no longer in axial alignment with the needle and the TAD. Thus, the need remains for a TAD for use with an epidural catheter (whether reinforced or not) which enables movement of the catheter slidingly along the needle without deflecting the catheter from the needle axis.

Accordingly, it is an object of the present invention to provide a catheter which does not require a stylet for the insertion operation.

Another object is to provide such a catheter which is economical to produce.

A further object is to provide a thread assist device (TAD) to facilitate passage of a catheter through a needle.

SUMMARY OF THE INVENTION

In one aspect, the present invention relates to a stylet-free catheter for insertion into a patient via a needle, wherein the needle defines proximally a needle hub and distally a needle tip. The catheter comprises a proximal end, a distal end, and a body connecting the proximal and distal ends. The body defines therealong a stiffening section of a predetermined length disposed a predetermined distance proximally of the distal end such that it is located generally about an area where the body approaches the needle hub when the distal end approaches the needle tip. The stiffening section has a flexural stiffness at least twice that of the remainder of the body.

In a preferred embodiment, the stiffening section has a length of about 5 (preferably 7) cm, disposed from about 10 cm to about 15 cm proximally of the distal end, and has a diameter not exceeding the diameter of the remainder of the body by more than about 0.15 mm.

In one preferred embodiment, the stiffening section is formed of plastic tubing and a cured adhesive extending circumferentially about the plastic tubing to provide a stiffening coating. The cured adhesive preferably is UV-cured in situ. In an alternatively preferred embodiment, the stiffening section is formed of plastic tubing and a plastic sleeve heat-shrunk about the plastic tubing to stiffen the plastic tubing. The sleeve is preferably polyethylene terephthalate (PET). In both preferred embodiments, the stiffening coating/sleeve is non-tacky and wear-resistant, has a thickness not exceeding about 0.08 mm, extends in a substantially uniform thickness along the stiffening section and about the plastic tubing, and reinforces the plastic tubing of the stiffening section.

The present invention also encompasses in combination such a catheter and a needle defining proximally a needle hub and distally a needle tip.

The present invention further encompasses a thread assist device to reduce buckling of a catheter being inserted through a needle. The TAD comprises a body defining a proximal end, a distal end substantially spaced along a longitudinal axis form the proximal end, and a sidewall connecting the proximal and distal ends. The TAD distal end is configured and dimensioned for at least partial receipt and releasable maintenance within a hub of a needle, and the TAD sidewall is configured and dimensioned to enable axial sliding manipulation of a catheter through the needle hub and through the needle by a user. The TAD proximal and distal ends substantially preclude non-axial or lateral movement of the catheter at the TAD ends, and the TAD sidewall limits non-axial or lateral movement of the catheter between the TAD ends. In a preferred embodiment, the TAD sidewall is generally cylindrical but extends no more than 180° about the TAD body intermediate the TAD proximal and distal ends to define a gap intermediate its long edges such that a user can establish axial sliding manipulation of the catheter through the gap and further limit non-axial movement of the catheter between the TAD ends.

In another embodiment, the TAD sidewall extends over an arc of no more than about 90° about the TAD body intermediate the TAD ends and is slightly bowed outwardly from the TAD longitudinal axis for substantially the entire length of the TAD sidewall along the catheter, thereby to increase the potential extent of contact between the user and the catheter between the TAD ends and thus facilitate grasping and generally axial movement of the catheter through the TAD by the user.

The present invention also encompasses in combination such thread assist device, a catheter, and a needle, the distal end of the TAD being at least partially disposed in the hub of the needle, and the catheter extending through the TAD proximal end, along the TAD sidewall, through the TAD distal end and into the needle.

Further, the present invention specifically encompasses the combination of such a catheter and such a TAD.

BRIEF DESCRIPTION OF THE DRAWING

The above and related objects, features, and advantages of the present invention will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Referring now to the drawing, and in particular FIGS. 1–6 thereof, therein illustrated is a stylet-free epidural catheter according to the present invention, generally designated by the reference numeral 10. The catheter 10 is designed for insertion into a patient via a needle, generally designated 12, defining proximally a needle hub 14, distally a needle tip 16 and optionally a pair of wings 17.

In its conventional aspects, the catheter 10 includes a proximal end 22, a distal end 24 and a body section, generally designated 26, connecting the proximal and distal ends 22, 24.

Figures 1, 2:
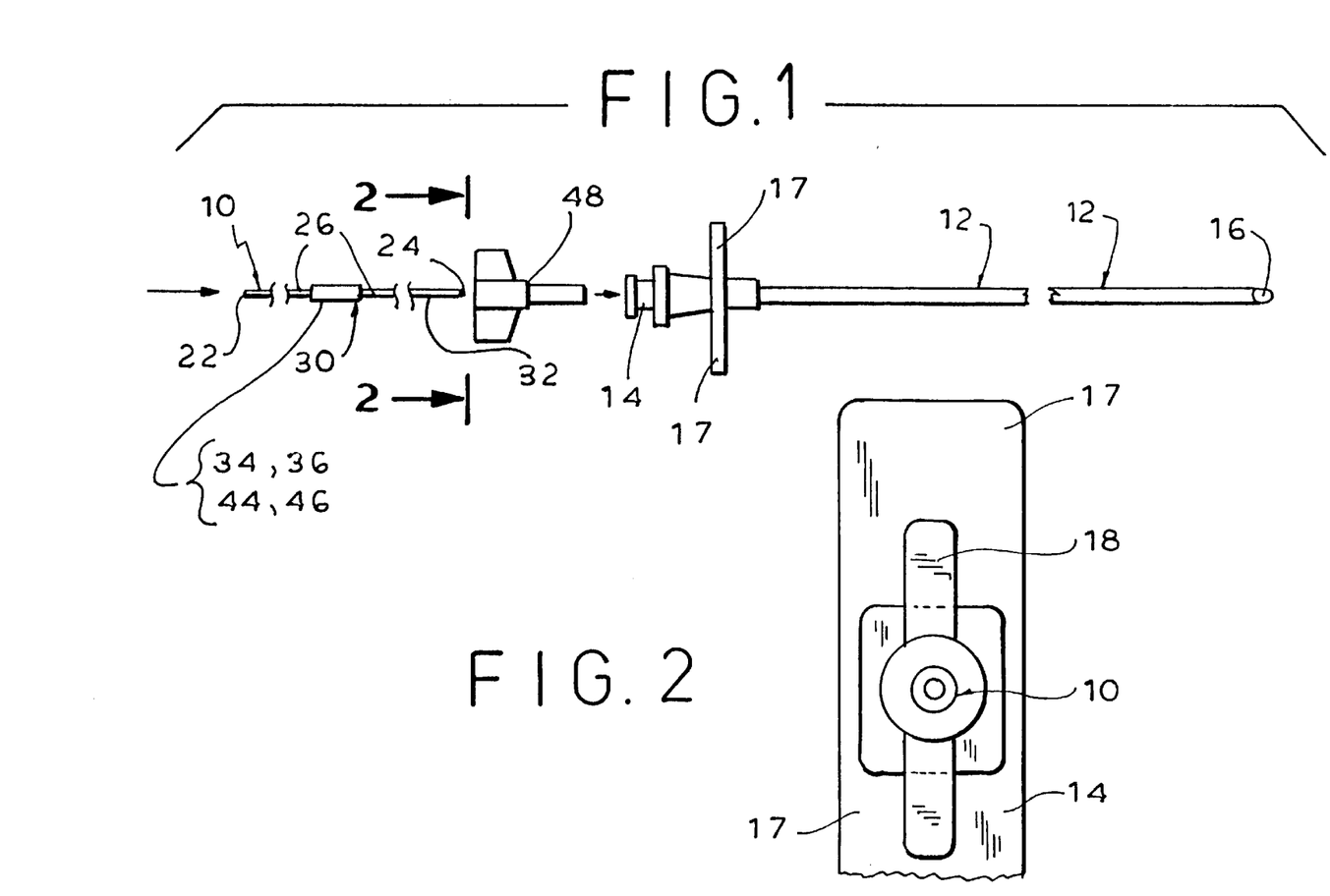
FIG. 1 is a fragmentary exploded side elevational view of a stylet-free epidural catheter according to the present invention.
FIG. 2 is a sectional view thereof taken along the line 2—2 of FIG. 1.
Figure 3:
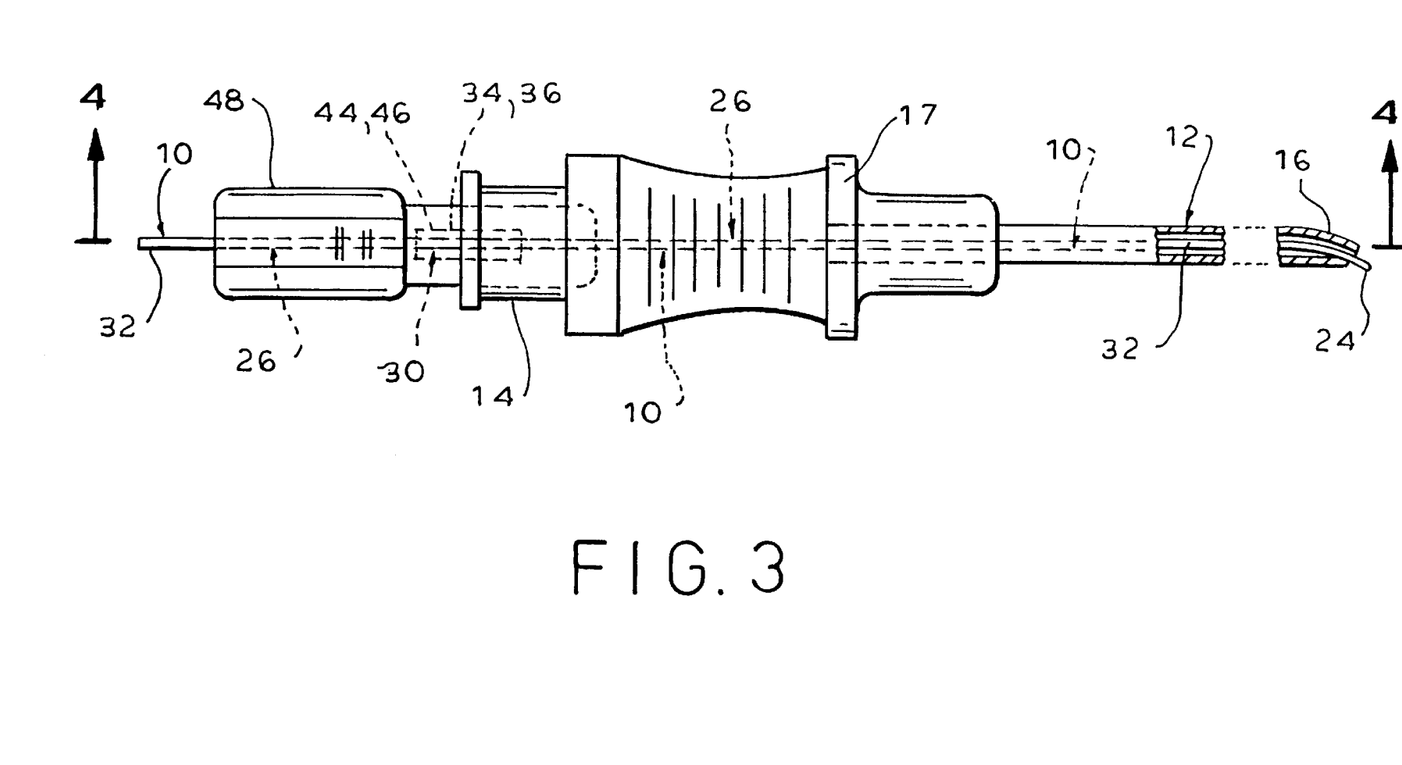
FIG. 3 is a fragmentary assembly side elevational view of the catheter rotated 90° about its axis from FIG. 1.
Figure 4:
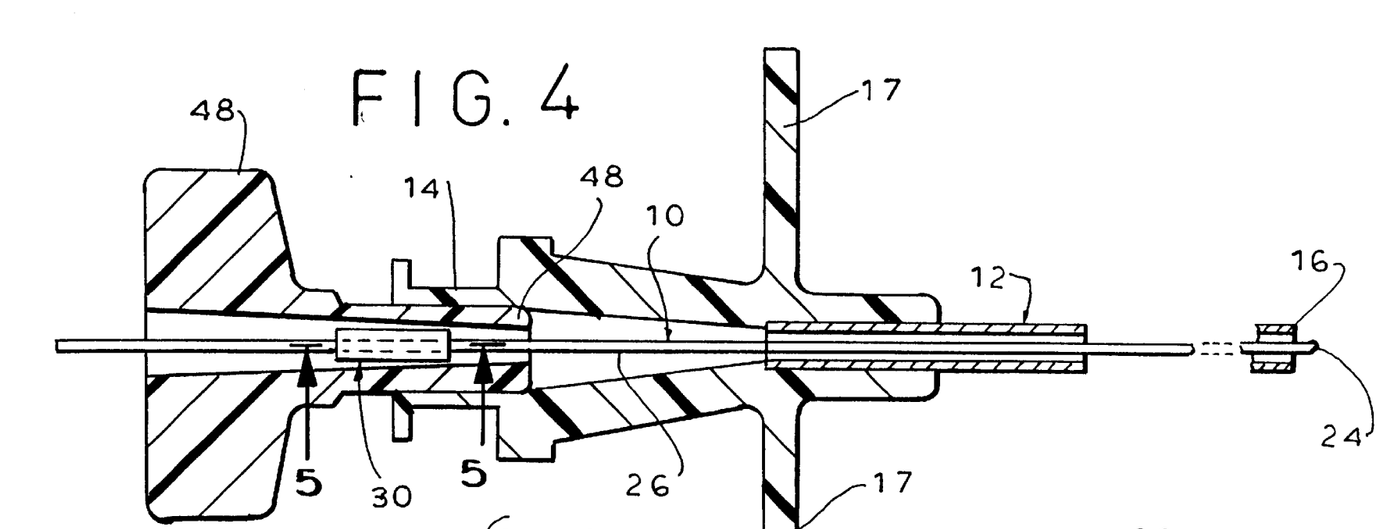
FIG. 4 is a sectional view thereof taken along the line 4—4 of FIG. 3.
Figure 5:
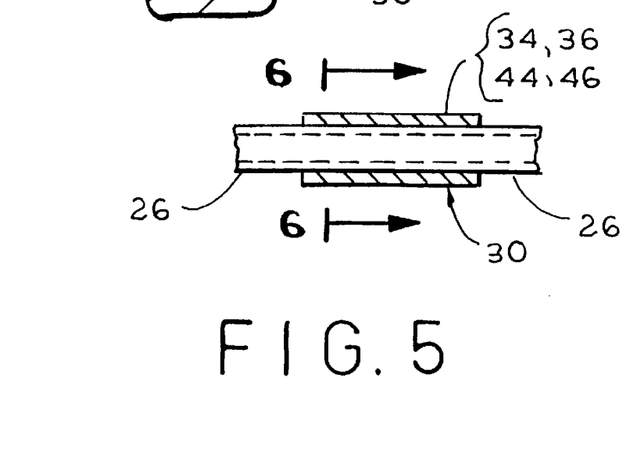
FIG. 5 is a sectional view thereof taken along the line 5—5 of FIG. 4.
Figure 6:
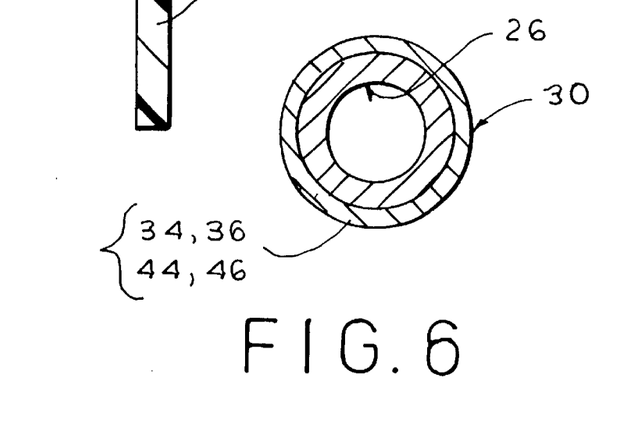
FIG. 6 is a sectional view taken along the line 6—6 of FIG. 5.
Figures 7, 8:
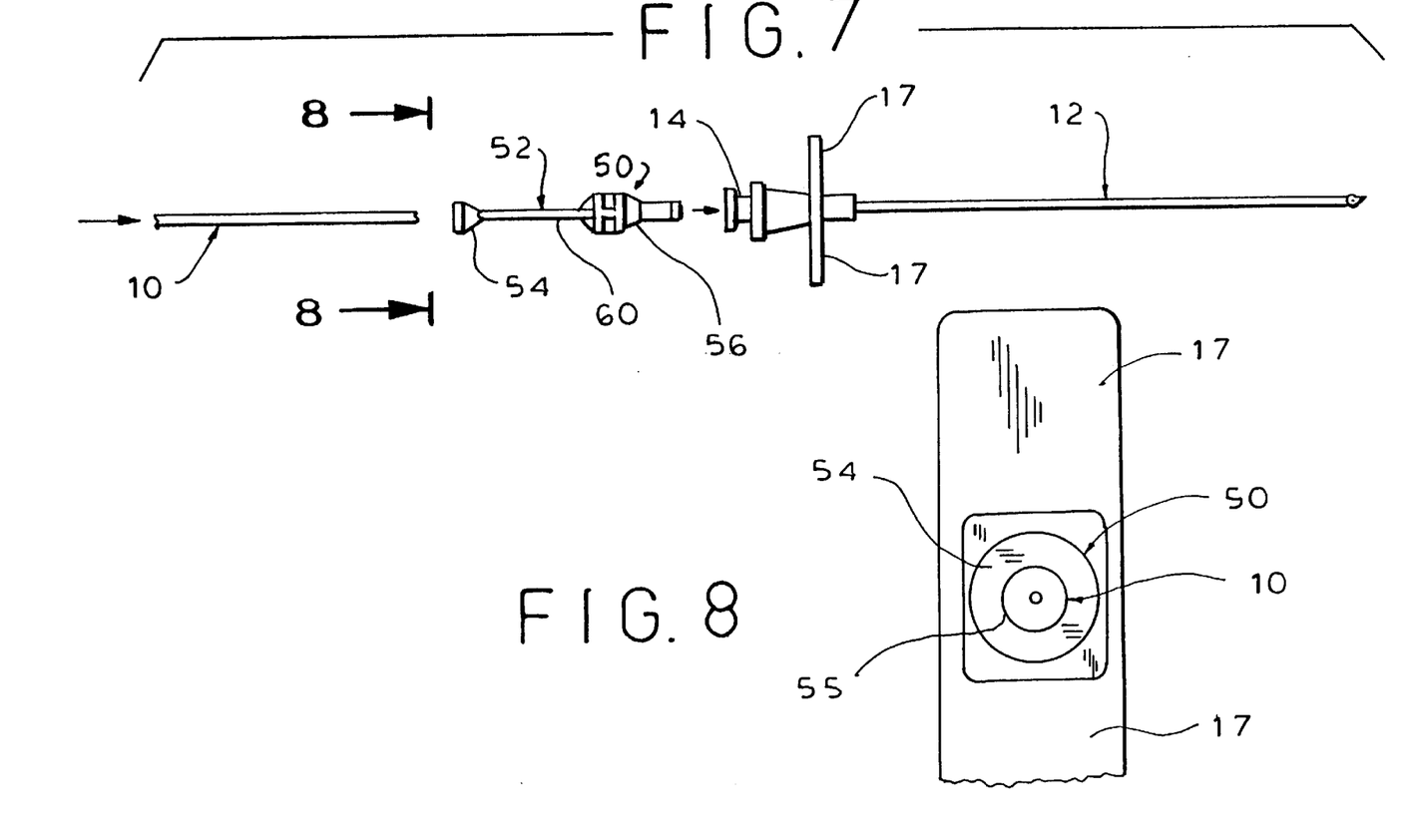
FIG. 7 is a fragmentary exploded side elevational view of a thread assist device according to the present invention.
FIG. 8 is a sectional view taken along the line 8—8 of FIG. 7.
Figure 9:
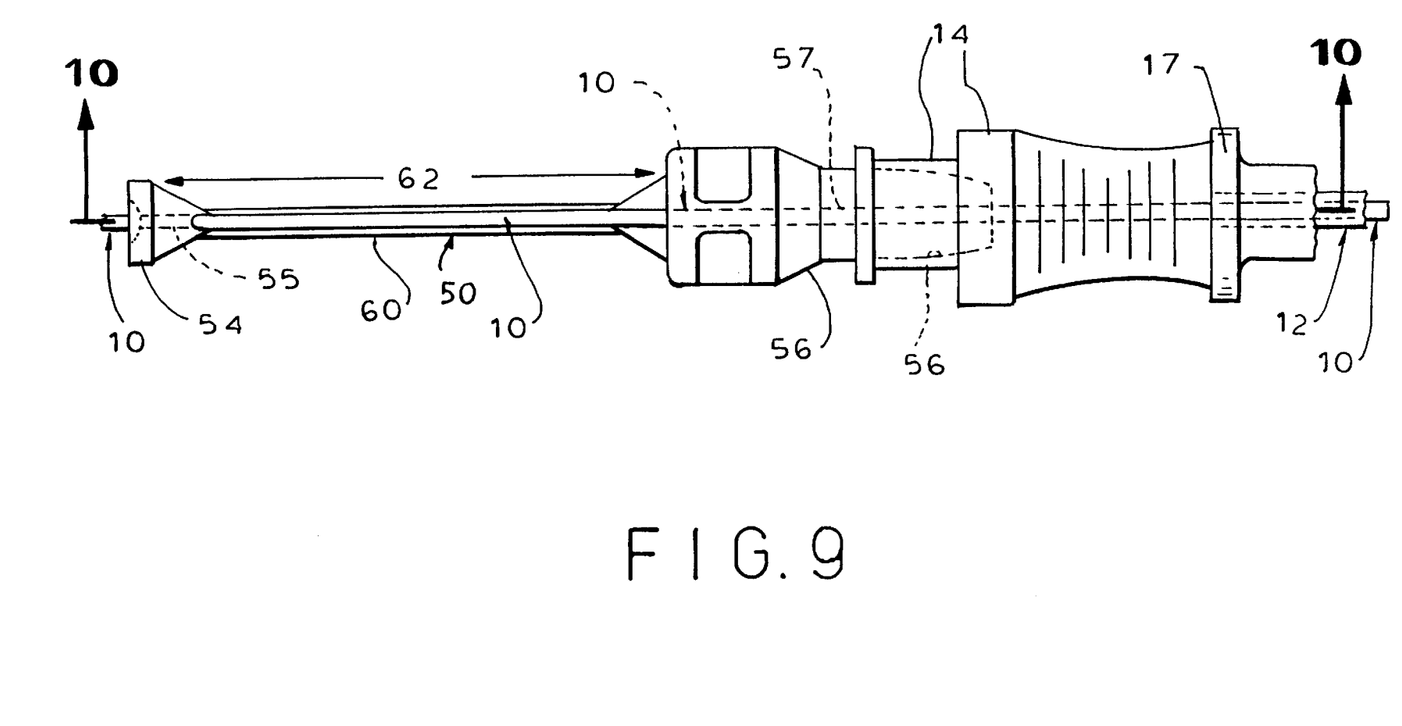
FIG. 9 is a fragmentary assembly side elevational view of the TAD rotated 90° about its axis from FIG. 7.

In its novel aspects, the body 26 of catheter 10 defines therealong a stiffening section, generally designated 30. The stiffening section 30 is of a predetermined length (preferably about 5 cm) and is disposed a predetermined distance proximally of the distal end 24 (preferably from about 10 cm to about 15 cm proximally of the distal end) such that it is located generally about an area where the catheter body 26 approaches the needle hub 14 when the catheter distal end 24 approaches the needle tip 16. This is a critical point in the functioning of the epidural device because, as the catheter distal end 24 begins to emerge from the distal needle tip 16, it encounters resistance which must be overcome by the surgeon sliding the catheter 10 through the needle 12. The stiffening section 30 has a diameter not exceeding the diameter of the remainder of the body 26 by more than about 0.15 mm so that the increase in thickness at the stiffening section 30 is barely appreciable. As will be apparent to those skilled in the art, the length and positioning of the stiffening section 30 may be adjusted for use in various epidural needles (for example, needles for different species), with the object always being that the strengthening section will be entering the needle hub as the catheter distal end is emerging from the needle tip.

It is a critical factor of the present invention that the stiffening section 30 has a flexural strength (that is, it resists non-axial or lateral bending) which is at least twice the flexural strength of the remainder of the catheter body 26. Flexural strength is easily measured using an Instron Tester. A minimum doubling of the flexural strength of the stiffening section (relative to the plastic tubing 32 alone of the remainder of the catheter body 26) obviates the need to employ a stylet in order to stiffen the catheter. Nonetheless, the stiffness of the stiffening section 30 must not preclude such bending thereof as may be necessary for it to pass through the curved needle tip 16. (Most needle tips are curved to facilitate passage therethrough of the catheter.) Further, the stiffening section 30 must not be so thick that it cannot pass through the needle 12 (and especially the needle tip 16).

The stiffening section 30 may be formed by various mechanisms.

In a first preferred mechanism illustrated in FIG. 1, the stiffening section 30 is formed of plastic tubing 32 (similar to the plastic tubing of the remainder of the catheter body 26) and a cured adhesive 34 extending circumferentially about the plastic tubing 32 to provide a stiffening coating 36. Preferably the stiffening coating 36 is non-tacky and is wear-resistant. The stiffening coating 36 preferably has a thickness not exceeding about 0.08 mm. Ideally, the stiffening coating 36 extends in a substantially uniform thickness along the stiffening section 30 and about the plastic tubing 32, so that it reinforces the plastic tubing 32 of the stiffening section 30. The cured adhesive is preferably a UV (ultraviolet)—cured adhesive tolerated by the patient's body, and optimally it is cured in situ. In other words, the uncured adhesive is applied about the plastic tubing 32 of the stiffening section 30 and then cured in place using ultraviolet light.

In a second preferred mechanism also illustrated in FIG. 1, the stiffening section 30 is formed of plastic tubing 32 (similar to the plastic tubing of the remainder of the catheter body 26) and a plastic sleeve 44 heat-shrunk about the plastic tubing 32 to provide a stiffening sleeve 46. As in the case of the stiffening coating 36, the stiffening sleeve 46 is preferably non-tacky and wear-resistant, has a thickness not exceeding 0.08 mm and ideally extends in a substantially uniform thickness along the stiffening section 30 and about the plastic tubing 32 so that the stiffening sleeve 46 reinforces the plastic tubing 32 of the stiffening section 30. The sleeve 44 may be made of any suitable heat-shrinkable plastic which is tolerated by the patient's body and provides the desired stiffening action when heat shrunk. A preferred plastic is polyethylene terephthalate (PET).

A conventional thread assist device (TAD) 48 has a front end which is inserted into the needle hub 14 and a rear end which is entered by the catheter front end 24, a length of the catheter body 26, the stiffening section 30 and more of the length of the catheter body 26.

Referring now to FIGS. 7–11 in particular, therein illustrated is a thread assist device (TAD) according to the present invention, generally 10 designated by the reference numeral 50, to reduce buckling (i.e., lateral or non-axial collapse) of a catheter being inserted through a needle 12, regardless of whether that catheter is a catheter 10 according to the present invention (as described hereinabove) or a conventional catheter. As the TAD 50 and stiffening section 30 serve the same function (that is, to reduce buckling of the catheter being inserted through the needle), typically the thread assist device finds greatest utility in use with a conventional catheter rather than a catheter 10 according to the present invention (as the latter typically does not require a TAD to be used).

The TAD 50 comprises a body, generally designated 52, defining a proximal end 54, a distal end 56, and a sidewall 60 connecting the TAD proximal and distal ends 54, 56. The TAD proximal and distal ends 54, 56 are substantially spaced apart along a longitudinal axis of the TAD body 52 and define respective full cylinder passageways 55, 57 therethrough, respectively. The distal end 56 of the TAD body 52 is configured and dimensioned for at least partial receipt and releasable maintenance within a needle hub 14.

Figure 10:
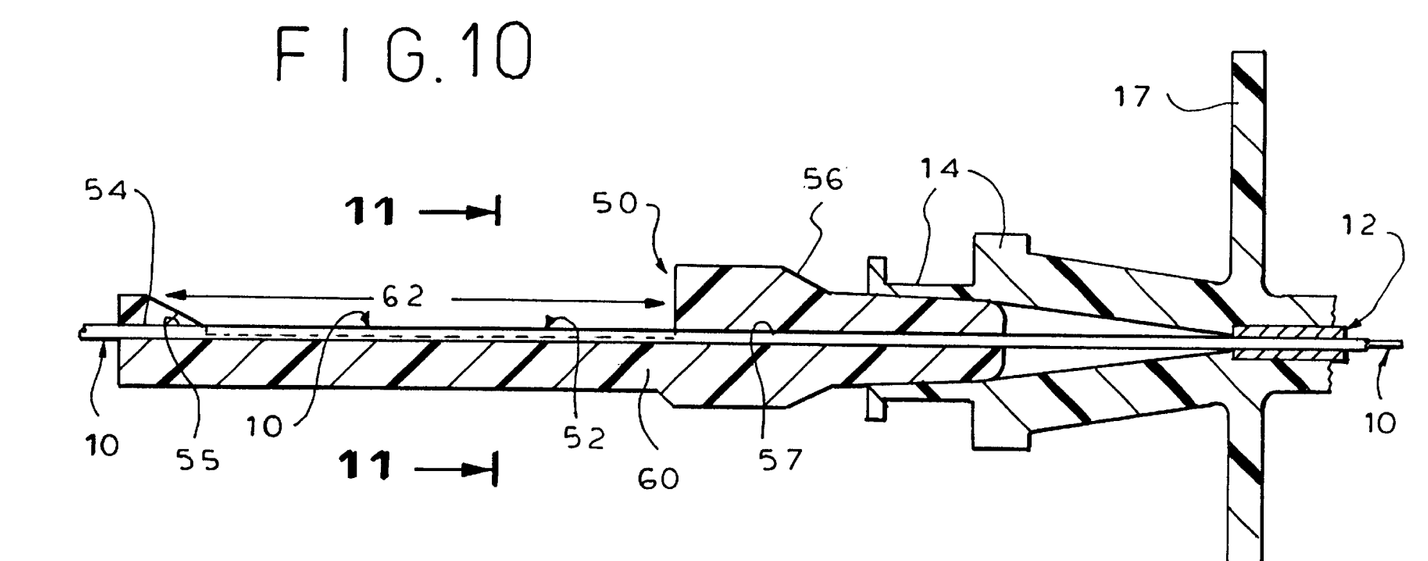
FIG. 10 is a sectional view thereof taken along the line 10—10 of FIG. 9.
Figure 11:
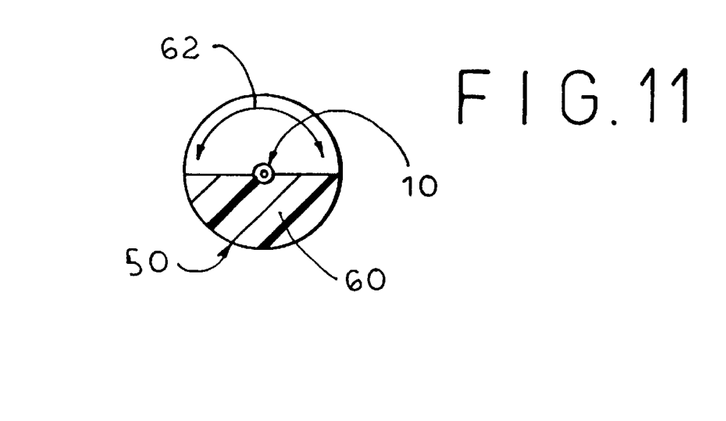
FIG. 11 is a sectional view thereof taken along the line 11—11 of FIG. 10.

The TAD sidewall 60 is configured and dimensioned intermediate the TAD proximal and distal ends 54, 56 to enable axial sliding manipulation of the catheter through the needle hub 14 by a user. More particularly, the sidewall 60 is generally cylindrical, but (as best seen in FIGS. 10 and 11) extends only about 180° (and clearly no more than 270°) about the TAD body 52 intermediate the TAD proximal and distal ends 54, 56 thereof. Thus the TAD sidewall 60 defines a gap 62 intermediate the long edges of the sidewall 60 subtending an angle of about 180° (and optionally less). This gap 62 is configured and dimensioned to enable a user to establish axial sliding manipulation of the catheter by inserting one or more fingers (or fingertips) through the gap 62 and against the catheter, thereby pressing the catheter against the TAD sidewall 60. The TAD proximal and distal ends 54, 56 substantially preclude non-axial movement of the catheter at the TAD ends, as such TAD ends extend fully about the circumference of the catheter portions extending therethrough. Because the pressure of the user's finger on the catheter only presses the catheter against the sidewall 60, the finger pressure further limits non-axial movement (buckling) of the catheter between the TAD ends 54, 56. The absence of any deflection of the catheter as it is being manipulated through the needle 12 facilitates the manipulation process by ensuring a common alignment of the longitudinal axes of the needle 12 and the catheter body 26.

Figures 12, 13:
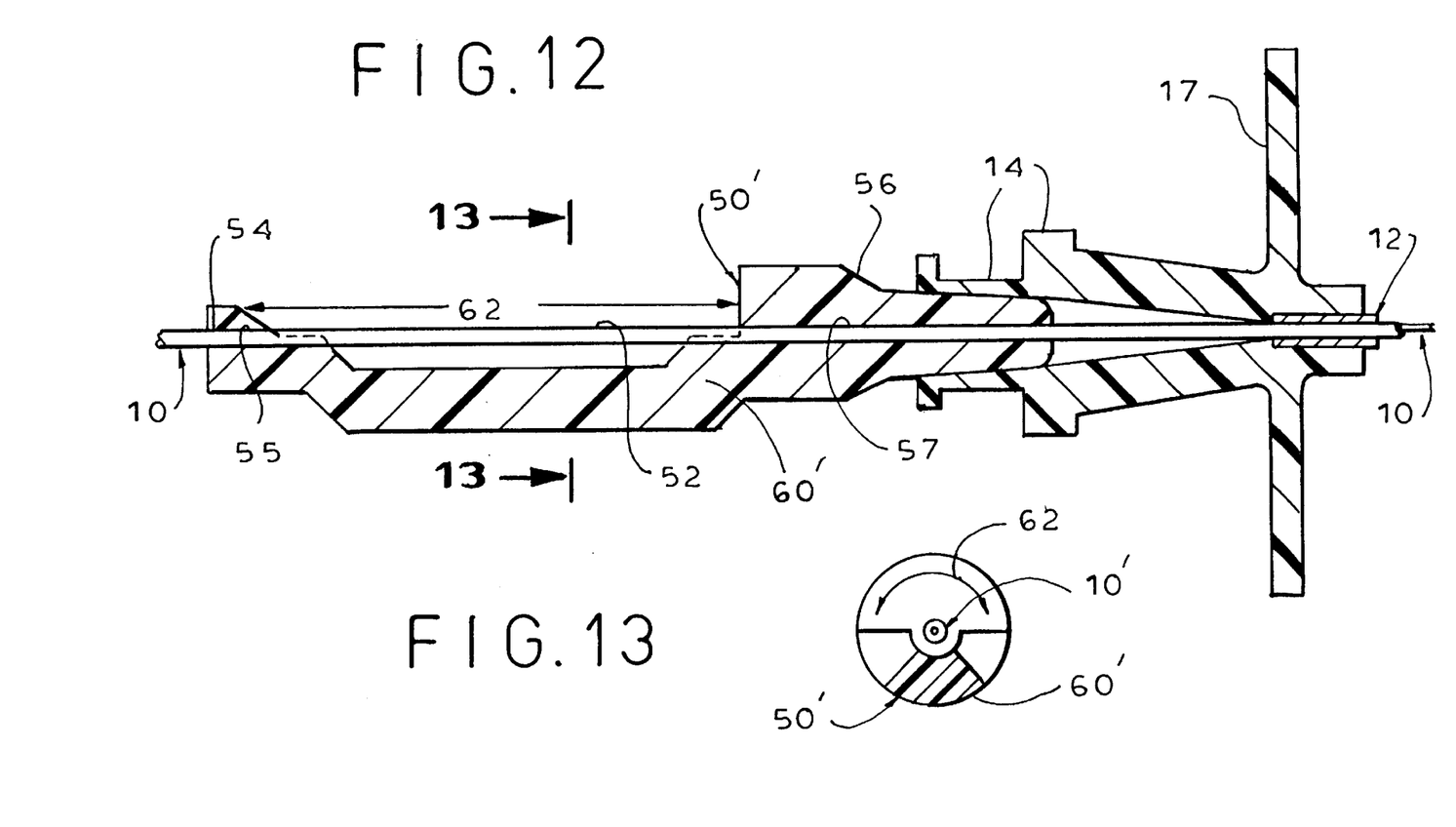
FIG. 12 is a view similar to FIG. 10, but of another embodiment of the TAD.
FIG. 13 is a sectional view thereof taken along the line 13—13 of FIG. 12.

Referring now to FIGS. 12 and 13, therein illustrated is a variant, generally designated 50', of the preferred TAD embodiment illustrated in FIGS. 7–11. The variant 50' is similar to the embodiment 50, except that in the variant 50' the TAD sidewall 60' defines a gap 62' subtending an angle of about 90° (and optionally less)—i.e., the sidewall 60' extends circumferentially about the catheter over an arc of no more than about 90° about the TAD body 52 intermediate the TAD ends 54, 56. Furthermore, in the variant 50', the TAD sidewall 60' is slightly bowed outwardly from the TAD longitudinal axis for substantially the entire length of the TAD sidewall 60' along the catheter. While the TAD proximal and distal ends 54, 56 still preclude buckling of the catheter therein, the lesser arc of the TAD sidewall 60' and the spacing of the TAD sidewall 60' from the unstressed catheter increases the potential extent of contact between one or more of the user's fingers and the catheter between the TAD ends 54, 56 as more of the catheter circumference is exposed and engageable by the user's fingertips. Accordingly, grasping and generally axial movement of the catheter through the variant TAD SO by the user is facilitated.

The TAD is preferably formed of a plastic, such as a medical grade thermoplastic material, which preferably exhibits a low flexural modulus in order to allow the TAD to be bent by the practitioner's finger during the placement operation. A preferred material is a low-density polyethylene.

While the drawing illustrates the reinforced epidural catheter 10 in combination with a TAD 50, it will be appreciated that the TAD 50 may be used with catheters other than the catheter 10 of the present invention.

To summarize, the present invention provides a stylet-free catheter which is economical to produce. The present invention further provides a thread assist device (TAD) to facilitate passage of a catheter (whether reinforced or not) through a needle.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

We claim:

1. A thread assist device (TAD) to reduce buckling of a catheter being inserted through a needle, said device comprising:

a TAD body defining a proximal end, a distal end substantially spaced apart along a longitudinal axis from said TAD proximal end, and a sidewall connecting said TAD proximal and distal ends;

said TAD distal end being configured and dimensioned for at least partial receipt and releasable maintenance within a hub of a needle;

said TAD sidewall being configured and dimensioned intermediate said TAD proximal and distal ends to define an aperture through said sidewall for enabling axial sliding manipulation of a catheter through the needle hub by a user via said aperture;

said TAD proximal and distal ends limiting non-axial movement of the catheter at said TAD ends and said TAD sidewall limiting non-axial movement of the catheter between said TAD ends.

2. The TAD of claim 1 wherein said TAD sidewall extends over an arc of no more than 90° about said TAD body intermediate said TAD ends and is slightly bowed outwardly from said TAD longitudinal axis for substantially the entire length of said TAD sidewall along the catheter, thereby to increase the potential extent of contact between the user and the catheter between said TAD ends and thus facilitate grasping and generally axial movement of the catheter through the TAD by the user.

3. The thread assist device of claim 1 wherein said TAD sidewall is configured and dimensioned intermediate said TAD proximal and distal ends to define a finger aperture through said sidewall for enabling manipulation of a catheter through the needle hub by the finger of a user via said aperture.

4. A combination including a thread assist device as set forth in claim 1, a catheter and a needle, said combination being characterized by said TAD distal end being at least partially disposed in a hub of said needle; and said catheter extending through said TAD proximal end, along said TAD sidewall, through said TAD distal end and into said needle.

5. The combination of claim 4 wherein said TAD sidewall is generally cylindrical but extends no more than 180° about said TAD body intermediate said TAD proximal and distal ends to define a gap intermediate its long edges such that a user can establish axial sliding manipulation of the catheter through said gap and further limit non-axial movement of the catheter between said TAD ends.

6. In combination, a stylet-free catheter and a thread assist device, comprising:

(A) a stylet-free catheter for insertion into a patient via a needle defining proximally a needle hub and distally a needle tip comprising:

a catheter having a proximal end, a distal end, and a body connecting said proximal and distal ends;

said body defining therealong a stiffening section of a predetermined length disposed a predetermined distance proximally of said distal end such that it is located generally about an area where said body approaches a needle hub when said distal end approaches a needle tip;

said stiffening section having a flexural stiffness at least twice that of the remainder of said body; and (B) a thread assist device to reduce buckling of said catheter being inserted through a needle, said TAD device comprising:

a body defining a TAD proximal end, a TAD distal end substantially spaced apart along a longitudinal axis from said TAD proximal end, and a TAD sidewall connecting said TAD proximal and distal ends;

said TAD distal end being configured and dimensional for at least partial receipt and releasable maintenance within a hub of a needle;

said TAD sidewall being configured and dimensioned intermediate said TAD proximal and distal ends to define an aperture through said sidewall for enabling axial sliding manipulation of said catheter through the needle hub by a user via said aperture;

said TAD proximal and distal ends substantially precluding non-axial movement of said catheter at said TAD ends and said TAD sidewall limiting non-axial movement of said catheter between said TAD ends.

7. The combination of claim 6 wherein the stiffening section distal end is spaced from the catheter distal end by the length of the needle.

* * * * *